United States Patent [19]

Zinke et al.

[11] Patent Number: 5,360,563
[45] Date of Patent: Nov. 1, 1994

[54] TRISAMIDODITHIONODIPHOSPATES

[75] Inventors: Horst Zinke, Reichelsheim/Odw., Germany; Rolf Schumacher, Marly, Switzerland

[73] Assignee: Ciba-Geigy Corporation, Ardsley, N.Y.

[21] Appl. No.: 68,369

[22] Filed: May 27, 1993

[30] Foreign Application Priority Data

Jun. 2, 1992 [CH] Switzerland ............... 1774/92-6

[51] Int. Cl.$^5$ ......................... C10M 137/16
[52] U.S. Cl. ........................ 252/46.7; 564/12; 564/14; 544/157; 546/21; 548/412; 252/78.5
[58] Field of Search ............. 252/46.7; 564/12, 14

[56] References Cited

FOREIGN PATENT DOCUMENTS

| | | | |
|---|---|---|---|
| 572954 | 3/1959 | Canada | 564/14 |
| 576426 | 5/1959 | Canada | 564/14 |
| 590102 | 1/1960 | Canada | 564/14 |
| 540782 | 5/1993 | European Pat. Off. . | |
| 1094745 | 4/1959 | Germany | 564/14 |
| 1412632 | 11/1975 | United Kingdom . | |
| 1598744 | 9/1981 | United Kingdom . | |
| WO-02045 | 2/1993 | WIPO . | |

*Primary Examiner*—Ellen M. McAvoy
*Attorney, Agent, or Firm*—Michele A. Kovaleski; Luther A. R. Hall

[57] ABSTRACT

There are disclosed compounds of formulae I and Ia

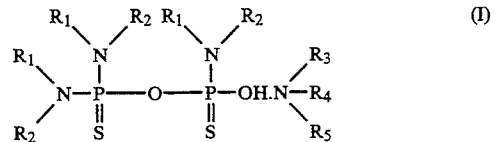

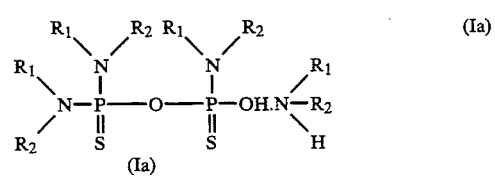

wherein $R_1$ and $R_2$ are each independently of the other $C_1$-$C_{13}$alkyl which may be interrupted by oxygen, $C_5$-$C_6$cycloalkyl or, together with the linking N-atom, are a group of formula

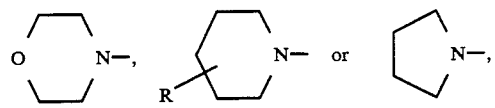

R is hydrogen or methyl,
$R_3$ is hydrogen or $C_1$-$C_{13}$alkyl, and
$R_4$ and $R_5$ are each independently of the other hydrogen, $C_1$-$C_{18}$alkyl which may be interrupted by oxygen, $C_5$-$C_6$cycloalkyl or, together with the linking N-atom, are a group of formula

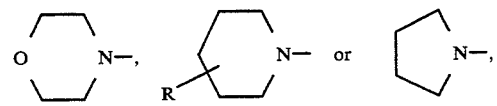

withe proviso that $R_3$, $R_4$ and $R_5$ are not simultaneously hydrogen and $HNR_1R_2$ are not identical with $NR_3R_4R_5$.

The compounds are suitable for use as lubricant additives.

12 Claims, No Drawings

TRISAMIDODITHIONODIPHOSPATES

The present invention relates to trisamidodithionophosphates, to a process for their preparation and to the use thereof as stabilisers and to compositions containing them.

GB 1 598 744 discloses flame retardants of formula

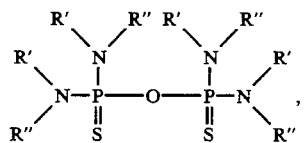

wherein R' and R" are unsubstituted or halogen-substituted alkyl, phenyl or benzyl radicals or, taken together, form heterocyclic rings containing an additional sulfur, nitrogen or oxygen atom.

The invention relates to novel compounds of formulae I and Ia

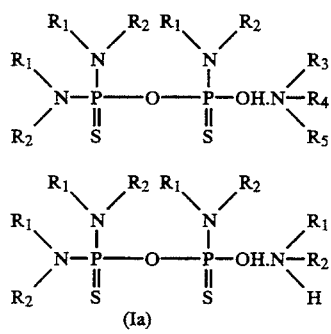

wherein $R_1$ and $R_2$ are each independently of the other $C_1$–$C_{13}$alkyl which may be interrupted by oxygen, $C_5$–$C_6$cycloalkyl or, together with the linking N-atom, are a group of formula

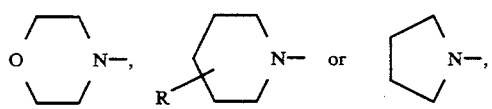

R is hydrogen or methyl,
$R_3$ is hydrogen or $C_1$–$C_{13}$alkyl, and
$R_4$ and $R_5$ are each independently of the other hydrogen, $C_1$–$C_{18}$alkyl which may be interrupted by oxygen, $C_5$–$C_6$cycloalkyl or, together with the linking N-atom, are a group of formula

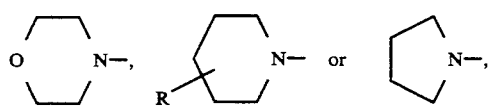

withe proviso that $R_3$, $R_4$ and $R_5$ are not simultaneously hydrogen and $HNR_1R_2$ are not identical with $NR_3R_4R_5$.

$R_1$, $R_2$ and $R_3$ defined as $C_1$–$C_{13}$alkyl may typically be methyl, ethyl, propyl, isopropyl, n-butyl, isobutyl, tert-butyl, pentyl, isopentyl, hexyl, heptyl, 3-heptyl, octyl, 2-ethylhexyl, nonyl, decyl, undecyl, dodecyl, tridecyl, 2-ethylbutyl, 1-methylpentyl, 1,3-dimethylbutyl, 1,1,3,3-tetramethylbutyl, 1-methylhexyl, isoheptyl, 1-methylheptyl, 1,1,3-trimethylhexyl or 1-methylundecyl.

$R_4$ and $R_5$ as $C_1$–$C_{18}$alkyl may additionally be tetradecyl, pentadecyl, hexadecyl, heptadecyl or octadecyl.

Alkyl radicals which are interrupted by —O— preferably contain the structural unit —$CH_2$—$CH_2$—O—. Illustrative examples of alkyl radicals of 1 to 8 carbon atoms will be found in the above list.

Radicals defined as $C_5$–$C_6$cycloalkyl will be taken to mean cyclopentyl or cyclohexyl.

$R_3$ is preferably hydrogen.

Preferred compounds are those wherein $R_1$ and $R_2$ are $C_1$–$C_8$alkyl, $C_5$–$C_6$cycloalkyl or, together with the linking N-atom, are a group of formula

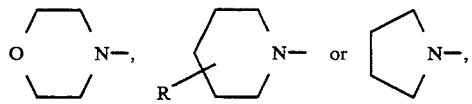

$R_3$ is hydrogen or $C_1$–$C_8$alkyl, and
$R_4$ and $R_5$ are hydrogen, $C_1$–$C_{18}$alkyl, $C_5$–$C_6$cycloalkyl or, together with the linking N-atom, are a group of formula

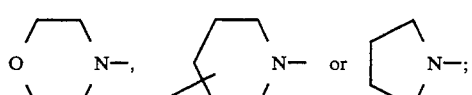

and also those wherein $R_1$ and $R_2$ are $C_1$–$C_8$alkyl or, together with the linking N-atom, are a group of formula

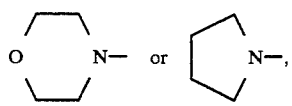

$R_3$ is hydrogen, and
$R_4$ and $R_5$ are hydrogen, $C_1$–$C_{18}$alkyl or, together with the linking N-atom, are a group of formula

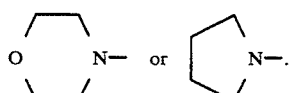

The compounds of formulae I and Ia are particularly suitable for use as lubricant additives.

The invention further relates to compositions comprising
a) a lubricant, a machining fluid or hydraulic fluid, and
b) at least one compound of formula I or Ia, the compounds referred to above as preferred resulting in preferred compositions.

The lubricants, machining fluids or hydraulic fluids contained in the inventive compositions can decompose readily to a greater or lesser degree under the action of heat, mechanical stress (especially induced by shear forces) and chemical reagents (especially atmospheric oxygen).

The compounds of formulae I and Ia afford protection against such influences and will conveniently be present in the novel compositions in amounts of 0.01 to 10% by weight, typically 0.05 to 5% by weight, preferably 0.05 to 3% by weight and, most preferably, 0.1 to 2% by weight. The novel compositions may contain one or more than one of these compounds, and the percentages by weight are based on the total amount of said compounds. The basis of calculation is the total weight of the lubricant, machining fluid or hydraulic fluid without the compounds of formula I and Ia.

The invention thus also relates to the use of compounds of formulae I and Ia as additives for lubricants, hydraulic fluids and machining fluids, especially as extreme-pressure and antiwear additives as well as friction modifiers.

Such a utility also entails a process for enhancing the performance properties of lubricants, hydraulic fluids and machining fluids. The novel utility also encompasses the protection of the metal pans to be lubricated against mechanical wear (antiwear protection).

The suitable lubricants, hydraulic fluids and machining fluids are typically based on mineral or synthetic oils or mixtures thereof. The lubricants are known to the skilled person and are described in the relevant literature, inter alia in Dieter Klamann, "Schmierstoffe und verwandte Produkte" (Lubricants and Related Products) (Verlag Chemie, Weinheim, 1982), in Schewe-Kobek, "Das Schmiermittel-Taschenbuch" (Handbook of Lubricants) (Dr. Alfred Hüthig-Verlag, Heidelberg, 1974), and in "Ullmanns Enzyklopädie der technischen Chemie" (Ullmann's Encyclopedia of Industrial Chemistry), Vol. 13, pages 85–94 (Verlag Chemie, Weinheim, 1977).

The lubricants are preferably oils and fats are typically derived from a mineral oil. Oils are preferred.

A further group of lubricants suitable for use in the practice of this invention comprises vegetable or animal oils, fats, tallows and waxes or mixtures with one another or with the mineral or synthetic oils referred to above. Vegetable and animal oils, fats, tallows and waxes are typically palm nut oil, palm oil, olive oil, beet oil, rapeseed oil, linseed oil, ground nut oil, soybean oil, cottonseed oil, sunflower seed oil, pumpkin seed oil, coconut oil, corn oil, castor oil, walnut oil and mixtures thereof, fish oils, the tallows of slaughter animals, e.g. beef tallow, neat's foot and bone oil, as well as the modified, epoxidised and sulfoxidised forms thereof, typically epoxidised soybean oil.

The mineral oils are based in particular on hydrocarbon compounds.

Synthetic lubricants typically comprise lubricants based on aliphatic or aromatic carboxylates, polymeric esters, polyalkylene oxides, phosphates, poly-α-olefins or silicones, on a diester of a divalent acid with a monohydric alcohol, typically dioctyl sebacate or dinonyl adipate, on a triester of trimethylolpropane with a monovalent acid or with a mixture of acids, conveniently trimethylolpropane tripelargonate, trimethylolpropane tricaprylate or mixturtes thereof, on a tetraester of pentaerythritol with a monovalent acid or with a mixture of such acids, typically pentaerythritol tetracaprylate, or on a complex ester of monovalent and divalent acids with polyhydric alcohols, for example a complex ester of trimethylolpropane with caprylic and sebacic acid or of a mixture thereof. Especially suitable lubricants are, in addition to mineral oils, typically poly-α-olefins, ester-based lubricants, phosphates, glycols, polyglycols and polyalkylene glycols and mixtures thereof with water.

Machining fluids and hydraulic fluids can be prepared from the same substances as those described above in connection with the lubricants. Often they are also emulsions of such substances in water or other liquids.

The lubricating compositions of this invention are used, inter alia, for combustion engines, typically for motor vehicles powered by engines of the Otto-cycle, diesel, two-stroke, Wankel or orbital type.

The compounds of formulae I and Ia are readily soluble in lubricants, machining fluids and hydraulic fluids and are therefore especially suitable for use as additives for lubricants, machining fluids and hydraulic fluids. Their surprisingly good antiwear properties merit special mention.

The invention thus further relates to a process for enhancing the performance properties of lubricants, machining fluids and hydraulic fluids, which comprises adding thereto compounds of formulae I or Ia.

The compounds of formulae I and Ia can be blended with the lubricating compositions in a manner known per se. The compounds are, for example, readily soluble in oils. It is also possible to prepare a masterbatch, which can be diluted in accordance with consumption to suitable concentrations with the appropriate lubricant. In such cases, concentrations higher than 10% by weight are also possible.

The lubricants, machining fluids and hydraulic fluids of this invention may also contain other additives which are added for further enhancement of the basic properties. These further additives comprise antioxidants, metal deactivators, rust inhibitors, viscosity improvers, pour-point depressants, dispersants, detergents, other extreme-pressure and antiwear additives.

Illustrative examples of such further additives are:
Examples of Phenolic Antioxidants:
1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-dinonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.

2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol and 2,6-didodecylthiomethyl-4-nonylphenol.

3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate and bis-(3,5-di-tert-butyl-4-hydroxyphenyl) adipate.

4. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol) and 4,4'-bis-(2,6-dimethyl)-4-hydroxyphenyl) disulfide.

5. Alkylidene bisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)- phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis-(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis-(3'-tert-butyl-4'-hydroxyphenyl)butyrate], bis(3-tert-butyl-4-hydroxy-5-methylphenyl)dicyclopentadiene, bis[2-(3'-tert-butyl-2'hydroxy-5'-methylbenzyl)-6-tert-butyl-4-methylphenyl]terephthalate, 1,1-bis(3,5-dimethyl-2-hydroxyphenyl)butane, 2,2-bis(3,5-di-tert-butyl-4hydroxyphenyl)propane, 2,2-bis(5-tert-butyl-4-hydroxy-2-methylphenyl)-4-n-dodecylmercaptobutane and 1,1,5,5-tetra(5-tert-butyl-4-hydroxy-2-methylphenyl)pentane.

6. O-, N- and S-Benzyl compounds, for example 3,5,3',5'-tetra-tert-butyl-4,4'-dihydroxydibenzyl ether, octadecyl 4-hydroxy-3,5-dimethylbenzyl-mercaptoacetate, tris(3,5-di-tert-butyl-4-hydroxybenzyl)amine, bis(4-tert-butyl-3-hydroxy-2,6-dimethylbenzyl)-dithioterephthalate, bis(3,5-di-tert-butyl-4-hydroxybenzyl) sulfide and isooctyl 3,5-di-tert-butyl-4-hydroxybenzylmercaptoacetate.

7. Hydroxybenzylated malonates, for example dioctadecyl 2,2-bis(3,5-di-tert-butyl-2hydroxybenzyl)malonate, dioctadecyl 2(3-tert-butyl-4-hydroxy-5-methylbenzyl)malonate, didodecylmercaptoethyl 2,2-bis(3,5-di-tert-butyl-4-hydroxybenzyl)malonate and bis[4-(1,1,3,3-tetramethylbutyl)phenyl]2,2-bis(3,5-di-tert-butyl-4-hydroxybenzyl)malonate.

8. Aromatic hydroxybenzyl compounds, for example 1,3,5-tris(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene and 2,4,6-tris(3,5-di-tert-butyl-4-hydroxybenzyl)phenol.

9. Triazine compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)hexahydro-1,3,5-triazine and 1,3,5-tris(3,5-dicyclohexyl-4-hydroxybenzyl)isocyanurate.

10. Benzylphosphonates, for example dimethyl 2,5-di-tert-butyl-4-hydroxybenzylphosphonate, diethyl 3,5-di-tert-butyl-4-hydroxybenzylphosphonate, dioctadecyl 3,5-di-tert-butyl-4-hydroxybenzylphosphonate, dioctadecyl 5-tert-butyl-4-hydroxy-3-methylbenzylphosphonate and the calcium salt of monoethyl 3,5-di-tert-butyl-4-hydroxybenzylphosphonate.

11. Acylaminophenols, for example 4-hydroxylauranilide, 4-hydroxystearanilide and octyl N-(3,5-di-tert-butyl-4-hydroxyphenyl)carbamate.

12. Esters of β-(3,5-di-tert-butyl-4-hydroxyphenyl)propionic acid with mono- or polyhydric alcohols, for example with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane and 4-hydroxymethyl-1-phospha-2,6,7-trioxabicyclo[2.2.2]octane.

13. Esters of β-(5-tert-butyl-4-hydroxy-3-methylphenyl)propionic acid with mono- or polyhydric alcohols, for example with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis-(hydroxyethyl)oxamide, 3-thiaundecanol, 3-thiapentadecanol, trimethylhexanediol, trimethylolpropane and 4-hydroxymethyl-1-phospha-2,6,7-trioxabicyclo[2.2.2]octane.

14. Esters of β-(3,5-dicyclohexyl-4-hydroxyphenyl)propionic acid with mono- or polyhydric alcohols, for example with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis-(hydroxyethyl)oxamide, 3-thiaundecanol, 3-thiapentadecanol, trimethylhexanediol, trimethylolpropane and 4-hydroxymethyl-1-phospha-2,6,7-trioxabicyclo-[2.2.2]-octane.

15. Esters of 3,5-di-tert-butyl-4-hydroxyphenylacetic acid with mono- or polyhydric alcohols, for example with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane and 4-hydroxymethyl-1-phospha-2,6,7-trioxabicyclo[2.2.2]octane.

16. Amides of β-(3,5-di-tert-butyl-4-hydroxyphenyl)propionic acid, for example N,N'-bis-(3,5-di-tert-butyl-4-hydroxyphenylpropionyl)hexamethylenediamine, N,N'-bis(3,5-di-tert-butyl-4-hydroxyphenylpropionyl)trimethylenediamine and N,N'-bis(3,5-di-tert-butyl-4-hydroxyphenylpropionyl)hydrazine.

Examples of Aminic Antioxidants:

N,N'-diisopropyl-p-phenylenediamine, N,N'-di-sec-butyl-p-phenylenediamine, N,N'-bis(1,4-dimethylpentyl)op-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4- octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methyl-phenyl)amino]ethane, 1,2-bis(-phenylamino)propane, (o-tolyl)biguanide, bis[4-(1',3'-dimethylbutyl)phenyl]amine, tert-octylated N-phenyl-1-naphthylamine, a mixture of mono- and dialkylated tert-butyl/tert-octyldiphenylamines, a mixture of mono- and dialkylated isopropyl/isohexyldiphenylamines, mixtures of mono- and dialkylated tert-butyldiphenylamines, 2,3-dihydro-3,3-dimethyl-4H-1,4-benzothiazine, phenothiazine, N-allylphenothiazine, N,N,N',N'-tetraphenyl-1,4-diaminobut-2-ene, N,N-bis(2,2,6,6-tetramethylpiperid-4-yl-hexamethylenediamine, bis(2,2,6,6-tetramethylpiperid-b 4-yl) sebacate, 2,2,6,6-tetramethylpiperidin-4-one and 2,2,6,6-tetramethylpiperidin-4-ol.

Examples of Other Antioxidants:

Aliphatic or aromatic phosphites, esters of thiodipropionic acid or of thiodiacetic acid, or salts of dithiocarbamic or dithiophosphoric acid, 2,2,12,12-tetramethyl-5,9-dihydroxy-3,7, 11-trithiatridecane and 2,2,15,15-tetramethyl-5,12-dihydroxy-3,7,10,14-tetrathiahexadecane.

Examples of Metal Deactivators, for Example for Copper, are:

a) Benzotriazoles and derivatives thereof, for example 4- or 5-alkylbenzotriazoles (e.g. tolutriazole) and derivatives thereof, 4,5,6,7-tetrahydrobenzotriazole and 5,5'-methylenebisbenzotriazole; Mannich bases of benzotriazole or tolutriazole, e.g. 1-[bis(2-ethylhexyl)aminomethyl]tolutriazole and 1-[bis(2-ethylhexyl)aminomethyl]benzotriazole; and alkoxyalkylbenzotriazoles such as 1-(nonyloxymethyl)benzotriazole, 1-(1-butoxyethyl)benzotriazole and 1-(1-cyclohexyloxybutyl)tolutriazole.

b) 1,2,4-Triazoles and derivatives thereof, for example 3-alkyl(or aryl)-1,2,4-triazoles, and Mannich bases of 1,2,4-triazoles, such as 1-[bis(2-ethylhexyl)aminomethyl-1,2,4-triazole; alkoxyalkyl-1,2,4-triazoles such as 1-(1-butoxyethyl)-1,2,4-troazole; and acylated 3-amino-1,2,4-triazoles.

c) Imidazole derivatives, for example 4,4'-methylenebis(2-undecyl-5-methylimidazole) and bis[(N-methyl)imidazol-2-yl]carbinol octyl ether.

d) Sulfur-containing heterocyclic compounds, for example 2-mercaptobenzothiazole, 2,5-dimercapto-1,3,4-thiadiazole and derivatives thereof; and 3,5-bis[di(2-ethylhexyl)aminomethyl]-1,3,4-thiadiazolin-2-one.

e) Amino compounds, for example salicylidenepropylenediamine, salicylaminoguanidine and salts thereof.

Examples of Rust Inhibitors are:

a) Organic acids, their esters, metal salts, amine salts and anhydrides, for example alkyl- and alkenylsuccinic acids and their partial esters with alcohols, diols or hydroxycarboxylic acids, partial amides of alkyl- and alkenylsuccinic acids, 4-nonylphenoxyacetic acid, alkoxy- and alkoxyethoxycarboxylic acids such as dodecyloxyacetic acid, dodecyloxy(ethoxy)acetic acid and the amine salts thereof, and also N-oleoylsarcosine, sorbitan monooleate, lead naphthenate, alkenylsuccinic anhydrides, for example dodecenylsuccinic anhydride, 2-(carboxyethyl)-1-dodecyl-3-methylglycerol and the amine salts thereof.

b) Nitrogen-containing compounds, for example:
   I. Primary, secondary or tertiary aliphatic or cycloaliphatic amines and amine salts of organic and inorganic acids, for example oil-soluble alkylammonium carboxylates, and also 1-[N,N-bis(2-hydroxyethyl)amino]-3-(4-nonylphenoxy)propan-2-ol.
   II. Heterocyclic compounds, for example: substituted imidazolines and oxazolines, and 2-heptadecenyl-1-(2-hydroxyethyl)imidazoline.

c) Phosphorus-containing compounds, for example: Amine salts of phosphoric acid partial esters or phosphonic acid partial esters, and zinc dialkyldithiophosphates.

d) Sulfur-containing compounds, for example: barium dinonylnaphthalenesulfonates, calcium petroleum sulfonates, alkylthio-substituted aliphatic carboxylic acids, esters of aliphatic 2-sulfocarboxylic acids and salts thereof.

e) Glycerol derivatives, for example: glycerol monooleate, 1-(alkylphenoxy)-3-(2-hydroxyethyl)-glycerols, 1-(alkylphenoxy)-3-(2,3-dihydroxypropyl)glycerols and 2-carboxyalkyl-1,3-dialkylglycerols.

Examples of Viscosity Index Improvers are:

Polyacrylates, polymethacrylates, vinylpyrrolidone/methacrylate copolymers, polyvinylpyrrolidones, polybutenes, olefin copolymers, styrene/acrylate copolymers and polyethers.

Examples of Pour-Point Depressants are:

Polymethacrylate and alkylated naphthalene derivatives.

Examples of Dispersants/Surfactants are:

Polybutenylsuccinic amides or -imides, polybutenylphosphonic acid derivatives and basic magnesium, calcium and barium sulfonates and phenolates.

Examples of Antiwear Additives are:

Sulfur- and/or phosphorus- and/or halogen-containing compounds, e.g. sulfurised olefins and vegetable oils, zinc dialkyldithiophosphates, alkylated triphenyl phosphates, tritolyl phosphate, tricresyl phosphate, chlorinated paraffins, alkyl and aryl di- and trisulfides, amine salts of mono- and dialkyl phosphates, amine salts of methylphosphonic acid, diethanolaminomethyltolyltriazole, bis(2-ethylhexyl)aminomethyltolyltriazole, derivatives of 2,5-dimercapto-1,3,4-thiadiazole, ethyl 3-[(diisopropoxyphosphinothioyl)thio]propionate, triphenyl thiophosphate (triphenylphosphorothioate), tris-(alkylphenyl) phosphorothioate and mixtures thereof (for example tris(isononylphenyl) phosphorothioate), diphenyl monononylphenyl phosphorothioate, isobutylphenyl diphenyl phosphorothioate, the dodecylamine salt of 3-hydroxy-1,3-thiaphosphetane 3-oxide, trithiophosphoric acid 5,5,5-tris[isooctyl 2-acetate], derivatives of 2-mercaptobenzothiazole such as 1-[N,N-bis-(2-ethylhexyl)aminomethyl]-2-mercapto-1H-1,3-benzothiazole, and ethoxycarbonyl-5-octyldithiocarbamate.

The compounds of this invention are prepared by methods which are known per se, conveniently in accordance with the following scheme:

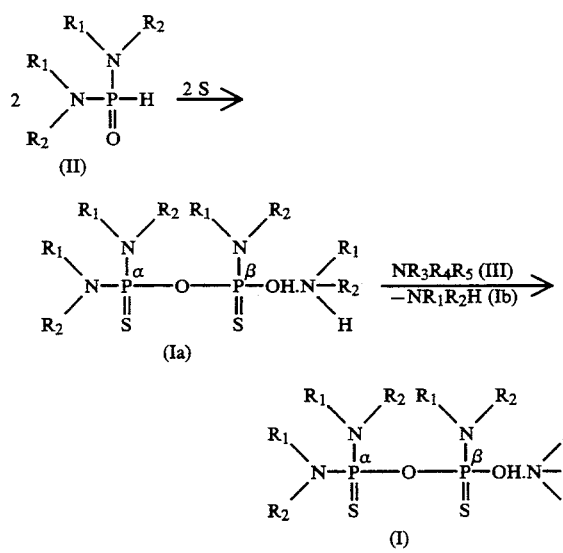

The invention thus also relates to a process for the preparation of compounds of formulae I and Ia, which comprises reacting an amide of formula II, preferably in a solvent, with sulfur, and, in an optional further step, with an amine of formula (III) to give the compound of formula I, the amines $HNR_1R_2$ and $NR_3R_4R_5$ not being identical.

The reaction with sulfur is exothermic, thereby necessitating cooling so that the temperature does not rise too steeply, preferably not above 85°–90° C. Normally the reaction is carried out in the temperature range from 0° to 90° C., preferably from 20° to 90° C., typically from 40° to 90° C. Suitable solvents are inert and also polar aprotic solvents (e.g. dimethyl formamide), preferably hydrocarbons with a suitable boiling point. Preferred solvents are aromatic hydrocarbons such as benzene and alkylated benzenes, typically xylene or toluene, preferably toluene.

The optional conversion of a compound of formula Ia into a compound of formula I can be carried out by methods commonly employed in chemistry (ion exchange), i.e. by treating a compound of formula Ia with an amine of formula III, with or without a solvent.

In a preferred embodiment of the invention, the amine of formula III has a higher boiling point than the compound $HNR_1R_2$ (Ib). Therefore to prepare compounds of formula I, a vacuum is applied once or repeatedly at room or slightly elevated temperature in the presence of the amine of formula III, so that Ib is expelled and the compound of formula I is formed. The amides of formula II are known per se (cf. DE-AS 1 125 425) or they can be prepared in general accordance with the method for obtaining the methyl compound described in "Methoden der organischen Chemie (Houben-Weyl) Vol. XII/2 (1964), Organische Phosphorverbindungen Teil 2", pp. 103–4.

Further particulars will be found in the following working Examples which illustrate the invention in more detail, but without implying any restriction to what is described therein. Unless otherwise indicated, parts and percentages are by weight.

EXAMPLE 1

Diethylammonium Trisdiethylamidodithionodiphosphate

Phosphorous acid bis(diethylamide)

With stirring and cooling, 13.8 g of phosphorous acid are added at a temperature below 40° C. to 35.2 g of phosphorous acid tris(diethylamide) (DE-AS 1 125 425) over 35 minutes. The mixture is stirred for a further 30 minutes at 35° C., for 15 minutes at 40° C. and for 15 minutes at 60° C. and left to stand overnight at room temperature. Subsequent distillation yields 30.1 g of an oil.

With stirring, 9.6 g (0.050 mol) of phosphorous acid bis(diethylamide) in 5 ml of toluene are added dropwise at 60°–80° C. to a suspension of 1.6 g (0.050 mol) of sulfur in 5 ml of toluene. The temperature of the exothermic reaction should not rise above 85°–90° C. After the sulfur has fully reacted, the reaction mixture is stirred for 1 hour at 90° C. The solvent is then removed by vacuum distillation at 60° C. Yield: 10.9 g (97% of theory) of a highly viscous, pale yellow liquid, $n_D^{20}$ 1.5170.

After treatment with isopropanol, 2.4 g of colourless crystals are isolated from the product which crystallises out after several days.

Melting point: 78°–80° C., % P calcd: 13.81, found: 13.75 $^{31}$P-NMR: $P_{60}\delta = 63.5$ ppm (d, $J_{P\text{-}O\text{-}P}37$ Hz), $P_\beta\delta = 52.6$ ppm (d, $J_{P\text{-}O\text{-}P}37$ Hz).

EXAMPLES 2–4

The compounds 2 to 4 listed in Table 1 are prepared in general accordance with the procedure described in Example 1:

TABLE 1

| | Compounds of formula Ia | | | | | |
|---|---|---|---|---|---|---|
| Example | $R_1R_2N-$ | $R_1R_2NH$ | $n_D^{20}$ | mp [°C.] | $P^\alpha$ [ppm/$H_3PO_4$] | $P^\beta$ [ppm/$H_3PO_4$] |
| 2 | Me$_2$N— | Me$_2$NH | 1.529 | 61–70 | 69.5 | 55.7 |
| 3 | O⟨N—⟩ (morpholino) | O⟨N—H⟩ (morpholine) | — | 59–64 | 62.7 | 51.8 |
| 4 | ⟨N—⟩ (pyrrolidino) | ⟨N—H⟩ (pyrrolidine) | 1.561 | — | 58.3 | 50.1 |

Me denotes methyl.

EXAMPLES 5 AND 6

(Table 2)

Example 6: 10.2 g (0.03 mol) of the compound of Example 2 are mixed with 12.55 g (0.03 mol) diisotridecylamine and 50 ml of toluene and the mixture is stirred for 1 hour at 80° C. Then the dimethylamine formed and the solvent are removed at 80° C. by vacuum distillation. Yield: 19.6 g (97% of theory of a yellow liquid.

TABLE 2

| | Compounds of formula I | | | | |
|---|---|---|---|---|---|
| Example | $R_1R_2N-$ | $R_3R_4R_5N$ | $n_D^{20}$ | mp [°C.] | $P^\alpha$[ppm/$H_3PO_4$] | $P^\beta$[ppm/$H_3PO_4$] |
| 5 | $Me_2N-$ | $(C_{13}H_{27})_2NH$ | 1.493 | — | 69.3 | 54.9 |
| 6 | $Me_2N-$ | $C_{18}H_{35}NH_2$ | 1.503 | — | 69.4 | 54.7 |

EXAMPLE 7

SRV Test

To test the antiwear and friction reducing properties, one of the novel compounds is incorporated in an undoped lubricating oil and the coefficient of friction $\mu$ is determined at 100° C. and 150° C. using the SRV apparatus (oscillating friction device supplied by Optimol GmbH, Munich; q.v. Lubrication Engineering 39 (11) 1982, Advert. Index cover 3, page 729).

In this method, an oscillating ball (50 Hz) is pressed with a force of 200N against a firmly clamped metal cylinder on which there is a film of test oil. The horizontal and vertical forces are measured with a piezoelectrical transducer. The signal so obtained is transmitted direct to the recorder. At the conclusion of the test, the cross-section of the wear scar on the metal cylinder is measured with a profilometer (TALYSURF 10). The test results are summarised in Table 3.

TABLE 3

| Additive* Cmpd of Example No. | Wear | | Coefficient of friction $\mu$ [mm²10⁻⁵]≠ | |
|---|---|---|---|---|
| | 100° C. | 150° C. | 100° C. | 150° C. |
| — | 85.2 | 217.4 | 0.121 | 0.122 |
| 5 | 29.8 | 45.4 | 0.094 | 0.111 |

*Additive concentration 1% in mineral oil, viscosity 139.3 mm²s⁻¹ at 40° C.
≠Cross-section of wear scar on the cylinder The low wear index and coefficient of friction relative to the undoped base oil demonstrate that the added compound has antiwear properties.

What is claimed is:
1. A compound of formula I or Ia

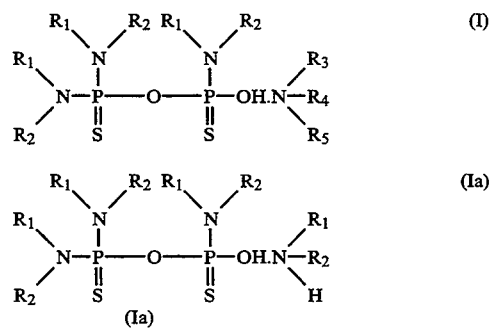

wherein $R_1$ and $R_2$ are each independently of the other $C_1$-$C_{13}$alkyl which may be interrupted by oxygen, $C_5$-$C_6$cycloalkyl or, together with the linking N-atom, are a group of formula

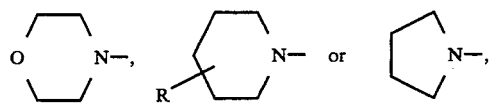

R is hydrogen or methyl, $R_3$ is hydrogen or $C_1$-$C_{13}$alkyl, and
$R_4$ and $R_5$ are each independently of the other hydrogen, $C_1$-$C_{18}$alkyl which may be interrupted by oxygen, $C_5$-$C_6$cycloalkyl or, together with the linking N-atom, are a group of formula

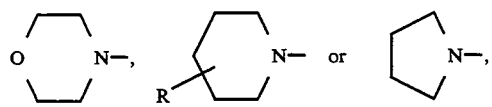

withe proviso that $R_3$, $R_4$ and $R_5$ are not simultaneously hydrogen and $HNR_1R_2$ are not identical with $NR_3R_4R_5$.

2. A compound according to claim 1, wherein $R_1$ and $R_2$ are $C_1$-$C_8$alkyl, $C_5$-$C_6$cycloalkyl or, together with the linking N-atom, are a group of formula

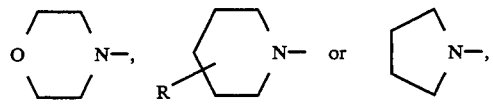

$R_3$ is hydrogen or $C_1$-$C_8$alkyl, and
$R_4$ and $R_5$ are hydrogen, $C_1$-$C_{18}$alkyl, $C_5$-$C_6$cycloalkyl or, together with the linking N-atom, are a group of formula

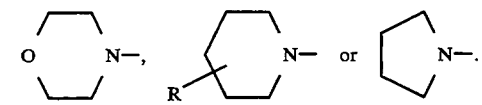

3. A compound according to claim 2, wherein $R_1$ and $R_2$ are $C_1$-$C_8$alkyl or, together with the linking N-atom, are a group of formula

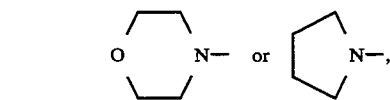

$R_3$ is hydrogen, and
$R_4$ and $R_5$ are hydrogen, $C_1$-$C_{18}$alkyl or, together with the linking N-atom, are a group of formula

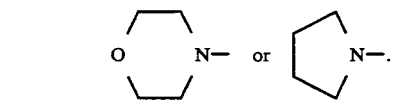

4. A process for the preparation of a compound of formula I or Ia as described in claim 1, which comprises reacting an amide of formula II

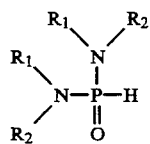

with sulfur, and, in an optional further step, with an amine of formula NR₃R₄R₅ to give the compound of formula I, the amines HNR₁R₂ and NR₃R₄R₅ not being identical.

5. A process according to claim 4, wherein the reaction with sulfur is carried out in the temperature range from 0° to 90° C.

6. A process according to claim 4, wherein the reaction is carried out in a solvent, preferably in toluene.

7. A composition comprising
   a) a lubricant, a machining fluid or hydraulic fluid, and
   b) at least one compound of formula I or Ia as claimed in claim 1.

8. A composition according to claim 7, which additionally comprises further stabilisers selected from the group consisting of antioxidants, metal deactivators, further extreme-pressure and antiwear additives and pour-point depressants.

9. A composition according to claim 7, wherein component a) is an engine oil.

10. A process for enhancing the performance properties of lubricant compositions, hydraulic fluids and machining fluids, which comprises adding thereto a compound of formula I or Ia as claimed in claim 1.

11. A composition according to claim 7, wherein component b) is at least one compound of formula I and R₁ and R₂ are C₁-C₈alkyl, C₅-C₆cycloalkyl or, together with the linking N-atom, are a group of formula

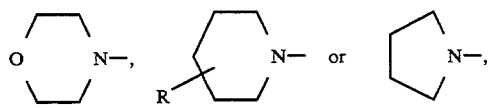

R₃ is hydrogen or C₁-C₈alkyl, and
R₄ and R₅ are hydrogen, C₁-C₁₈alkyl, C₅-C₆cycloalkyl or, together with the linking N-atom, are a group of formula

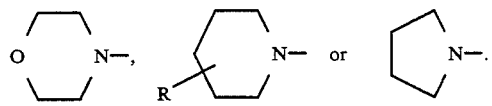

12. A composition according to claim 7, wherein component b) is at least one compound of formula I and R₁ and R₂ are C₁-C₈alkyl or, together with the linking N-atom, are a group of formula

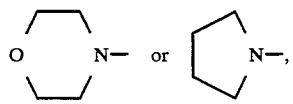

R₃ is hydrogen, and
R₄ and R₅ are hydrogen, C₁-C₁₈alkyl or, together with the linking N-atom, are a group of formula

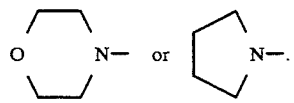

* * * * *